United States Patent
Dennis et al.

(10) Patent No.: US 8,580,852 B2
(45) Date of Patent: Nov. 12, 2013

(54) 2-OXAMIDE INHIBITORS OF PHOSPHOLIPASE A2 ACTIVITY AND CELLULAR ARACHIDONATE RELEASE BASED ON DIPEPTIDES AND PSEUDOPEPTIDES

(75) Inventors: Edward A. Dennis, La Jolla, CA (US); George Kokotos, Athens (GR); Violetta Constantinou-Kokotou, Athens (GR)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/262,618

(22) PCT Filed: Apr. 19, 2010

(86) PCT No.: PCT/US2010/031644
§ 371 (c)(1),
(2), (4) Date: Dec. 12, 2011

(87) PCT Pub. No.: WO2010/123832
PCT Pub. Date: Oct. 28, 2010

(65) Prior Publication Data
US 2012/0095096 A1   Apr. 19, 2012

Related U.S. Application Data

(60) Provisional application No. 61/171,002, filed on Apr. 20, 2009.

(51) Int. Cl.
*A61K 31/22* (2006.01)
*A61K 31/195* (2006.01)
*A61P 29/00* (2006.01)

(52) U.S. Cl.
CPC ................................. *A61K 31/22* (2013.01)
USPC ........... 514/551; 560/169; 560/170; 562/561; 562/567; 514/563

(58) Field of Classification Search
None
See application file for complete search history.

(56) References Cited

FOREIGN PATENT DOCUMENTS

WO    WO 2007/022443 A2  *  2/2007  ............. A61K 31/22

OTHER PUBLICATIONS

Barbayianni et al., "2-Oxamide Inhibitors of Phospholipase $A_2$ Activity and Cellular Arachidonate Release Based on Dipeptides and Pseudodipeptides," *Bioorg. Med. Chem.* (2009), 17(13):4833-4843, Elsevier Ltd.

Cheah et al., "Synthesis of Anti-Bacterial Peptidomimetics Derived from N-acylisatins," *Tetrahedron Lett.* (2008), 49(18):2965-2968, Elsevier Ltd.

Deska and Kazmaier, "Highly Stereoselective Peptide Modifications through Pd-Catalyzed Allylic Alkylations of Chelated Peptide Enolates," *Chem. Eur. J.* (2007), 13(21):6204-6211, Blackwell Science Ltd.

Kazmeier et al. "Highly Stereoselective Allylic Alkylations of Peptides," *Angew. Chem. Int. Ed.* (2006), 45(29):4855-4858, Wiley-VCH Verlag GmbH & Co. KGaA, Weinheim, Germany.

* cited by examiner

*Primary Examiner* — Jean C. Witz
*Assistant Examiner* — Mindy Newman
(74) *Attorney, Agent, or Firm* — DLA Piper LLP (US)

(57) ABSTRACT

The disclosure provides a series of 2-oxoamides based on dipeptides and pseudodipeptides, which were synthesized and their activities toward two human intracellular phospholipases A2 (GIVA CPLA 2 and GVIA 1PLA 2) and one human secretory phospholipase A2 (GV sPLA 2) were evaluated. Derivatives containing a free carboxyl group are selective GIVA cPLA 2 inhibitors. A derivative based on the ethyl ester of an ether pseudodipeptide is the first 2-oxoamide, which preferentially inhibits GVIA iPLA 2. The effect of 2-oxoamides on the generation of arachidonic acid from RAW 264.7 macrophages was also studied. It was found that selective GIVA cPLA 2 inhibitors preferentially inhibited cellular arachidonic acid release; in which one pseudodipeptide gave an IC50 value of 2 μM.

9 Claims, 3 Drawing Sheets

2-OXAMIDE INHIBITORS OF PHOSPHOLIPASE A2 ACTIVITY AND CELLULAR ARACHIDONATE RELEASE BASED ON DIPEPTIDES AND PSEUDOPEPTIDES

CROSS REFERENCE TO RELATED APPLICATIONS

This application is a 35 USC §371 National Stage application of International Application No. PCT/US2010/031644 filed Apr. 19, 2010, now pending; which claims the benefit under 35 USC §119(e) to U.S. Application Ser. No. 61/171,002 filed Apr. 20, 2009, now expired. The disclosure of each of the prior applications is considered part of and is incorporated by reference in the disclosure of this application.

GRANT INFORMATION

This invention was made with government support under Grant Nos. GM20501, GM64611 and U54 GM069338 (E.A.D.) awarded by the National Institutes of Health. The government has certain rights in the invention.

BACKGROUND OF THE DISCLOSURE

Tissue injury and inflammation lead to the development of an evident facilitation in the sensitivity to moderately aversive stimuli, e.g. hyperalgesia. It has been long appreciated that this phenomenon is diminished by agents that block cyclooxygenase (COX) activity (Vane, Nat. New Biol., 231: 232-235, 1971). While early work suggested that this action resulted from a peripheral effect (Ferreira, Nat. New Biol., 240:200-203, 1972), it was subsequently found that inhibition of spinal COX also led to reversal of the facilitated state (Yaksh, et al., "Acetylsalicilic Acid: New Uses for an Old Drug", pp. 137-152 (Barnet, et al., editors) Raven Press, 1982; Taiwo and Levine, J. Neurosci., 8:1346-1349, 1988). Consistent with this action, persistent small afferent input, as arises from tissue injury, was shown to evoke a significant spinal release of prostanoids in vivo in a mariner that was blocked by spinally-delivered COX inhibitors (Ramwell, et al., Am. J. Physiol., 211:998-1004, 1966; Yaksh, supra, 1982; Malmberg and Yaksh, Science, 257:1276-1279, 1992; Malmberg and Yaksh, J. Neurosci., 15:2768-2776, 1995; Ebersberger, et al., 1999, Samad et al., Nature, 410:471-475, 2001, and Yaksh, et al., J. Neurosci., 21:5847-5853, 2001). An important element of prostaglandin (PG) synthesis is phospholipase $A_2$ ($PLA_2$), as it is required to generate arachidonic acid, which is the substrate for COX-mediated prostanoid formation.

Phospholipase $A_2$ ($PLA_2$) constitutes a super-family of enzymes that catalyze the hydrolysis of the fatty acid ester from the sn-2 position of membrane phospholipids, yielding a free fatty acid and a lysophospholipid. Among the intracellular $PLA_2$, are the cytosolic Group IVA $PLA_2$ (GIVA $PLA_2$, also referred to herein as $cPLA_2$), which is generally considered a pro-inflammatory enzyme; the calcium-independent Group VIA $PLA_2$ (GVIA $PLA_2$, also referred to herein as $iPLA_2$); and, secreted Group V $PLA_2$ ($sPLA_2$). GVIA $PLA_2$ is actually a group of cytosolic enzymes ranging from 85 to 88 kDa and expressed as several distinct splice variants of the same gene, only two of which have been shown to be catalytically active (Group VIA-1 and VIA-2 $PLA_2$, see Larsson, et al., J. Biol. Chem. 273: 207-214, 1998). The role of GVIA $PLA_2$ in the inflammatory process is unclear, but this enzyme appears to be the primary $PLA_2$ for basal metabolic functions within the cell, reportedly including membrane homeostasis (Balsinde, et al., Proc. Natl. Acad. Sci. U.S.A., 92:8527-8531, 1995; Balsinde, et al., J. Biol. Chem., 272: 29317-29321, 1997; Balsinde, et al., J. Biol. Chem., 272:16069-16072, 1997; Ramanadham, et al., J. Biol. Chem., 274:13915-13927, 1999; Birbes, et al., Eur. J. Biochem., 267:7118-7127, 2000; and Ma, et al., Lipids, 36:689-700, 2001.), insulin receptor signaling (Ramanadham, et al., J. Biol. Chem., 274: 13915-13927, 1999; Ma, et al., J. Biol. Chem., 276: 13198-13208, 2001) and calcium channel regulation (Guo, et al., J. Biol. Chem., 277: 32807-32814, 2002; Cummings, et al., Am. J. Physiol. Renal Physiol., 283: F492-498, 2002). GVIA, GIVA and GV $PLA_2$ are all present and play active roles in central nervous system inflammatory processes (see, e.g., Sun, et al., J. Lipid Res., 45:205-213, 2004).

The GVIA $PLA_2$ enzymes all contain a consensus lipase motif, Gly-Thr-Ser*-Thr-Gly, with the catalytic serine confirmed by site-directed mutagenesis (Larsson, et al., J. Biol. Chem., 273:207-14, 1998; Tang, et al., J. Biol. Chem., 272: 8567-8575, 2002). Other residues critical for catalysis have yet to be confirmed, and while the mechanism by which it cleaves the sn-2 linkage has not been established, GVIA $PLA_2$ is likely to be an hydrolase with a catalytic Ser/Asp dyad similar to Group IVA $PLA_2$ (Dessen, et al., Cell 1999, 97: 349-360, 1999; Dessen, Biochim. Biophys. Acta, 1488: 40-47, 2000; Phillips, et al., J. Biol. Chem., 278: 41326-41332, 2003). Constitutive mRNA and protein have been detected in the spinal cord for group IVA calcium-dependent $PLA_2$ (Group IVA $cPLA_2$) and Group VIA calcium-independent $iPLA_2$ (Group VIA iPLA2) and secretory Group II and V $sPLA_2$ forms (Lucas, et al., Br. J. Pharmacol., 144:940-952, 2005, Svensson et al., Annu. Rev. Pharmacol. Toxicol., 42:553-555, 2005).

The discovery of a novel structural series of 2-oxoamides that inhibit Group IVA $cPLA_2$ in vitro and in vivo (Kokotos, et al., J. Med. Chem., 45:2891-2893, 2002; Kokotos, et al., J. Med. Chem., 47:3615-3628, 2004) was recently reported. In that initial work, 2-oxoamides were observed to inhibit inflammation in the rat paw carrageenan-induced edema assay (Kokotos, et al., supra, 2004). Based upon the similarity of substrates, classes of common inhibitors, very limited sequence homology in the region of the catalytic serine, and similarities in the active sites of GIVA and GVIA $PLA_2$, GIVA $PLA_2$ may show cross-reactivity with GVIA $PLA_2$. It has been difficult, however, to design selective inhibitors that can distinguish between these active sites in vivo. Thus, what is need in the art are selective Group IVA $cPLA_2$ in vitro and in vivo inhibitors.

SUMMARY OF THE DISCLOSURE

Phospholipase $A_2$ ($PLA_2$) enzymes catalyze the hydrolysis of the sn-2 ester bond of glycerophospholipids producing free fatty acids and lysophospholipids. The $PLA_2$ superfamily currently consists of fifteen groups and many subgroups of which a number of enzymes differ in primary sequence, structure and catalytic mechanism. The three predominant types of phospholipase $A_2$ ($PLA_2$) found in human tissues are the cytosolic (such as the GIVA $cPLA_2$), the secreted (such as the GV $sPLA_2$), and the calcium-independent (such as the GVIA $iPLA_2$) enzymes. GIVA $cPLA_2$ preferentially hydrolyzes membrane phospholipids containing arachidonic acid (AA), which is converted to a variety of proinflammatory eicosanoids. Thus, inhibiting AA release is of great therapeutic relevance for the development of new anti-inflammatory drugs. In many cases the activity of GIVA $cPLA_2$ has been shown to be dependent on or linked to the activity of $sPLA_2$.

GVIA iPLA$_2$ appears to be the primary phospholipase for basal metabolic functions within the cell, and perhaps has additional functions in specific cell types; however its role in inflammation is still unclear.

The disclosure provides a novel class of GIVA cPLA$_2$ inhibitors designed to contain the 2-oxoamide functionality and a free carboxyl group. 2-Oxoamides based on γ-aminobutyric acid (compound AX006, FIG. 1) and the non-natural amino acids γ-(S)-norleucine or δ-(S)-norleucine (compounds AX062 and AX109, FIG. 1) are potent inhibitors of GIVA cPLA$_2$ presenting in vivo anti-inflammatory and analgesic activity. In addition, the 2-oxoamide ethyl ester derivative AX048 (FIG. 1), which inhibits both GIVA cPLA$_2$ and GVIA iPLA$_2$ in vitro, presents a potent anti-hyperalgesic effect Most recently, there has been reported an amide based on γ-(R)-norleucine is a selective inhibitor of GV sPLA$_2$.

The present disclosure provides a variety of 2-oxoamides based on dipeptides and pseudodipeptides with inhibitory activity on one or more of three human PLA$_2$ classes: GIVA cPLA$_2$ (cPLA2), GVIA iPLA$_2$ (iPLA2), and GV sPLA$_2$ (sPLA2). The inhibitory compounds of the disclosure also impact cellular arachidonic acid release from RAW 264.7 macrophages.

The disclosure also provides potent inhibitors of phospholipase A$_2$ (PLA2), and methods for use of the inhibitory compounds, with particular emphasis on inhibitors that act more potently on, or are selective for, iPLA2. The PLAs are important to a number of inflammatory processes in mammals. For example, it has been discovered that PLA2 is both present and active in the spinal cord. More broadly, it is causatively related to spinally mediated inflammatory processes, suggesting a new method for treating inflammation, pain, hyperalgesia (pain experienced through hypersensitivity to stimulus), and other conditions causatively related to inflammation (e.g., neurological disorders stemming from inflammation affecting the central nervous system (CNS)). The disclosed inhibitory compounds are especially useful in treating these conditions, and act on PLA2, rather than on the cyclooxygenase enzymes. The PLA2 inhibitors of the disclosure are 2-oxoamide compounds which exhibit a high degree of specificity for both the cytosolic (cPLA2) and calcium-independent (iPLA2) isoforms of PLA2.

Thus, in one aspect the disclosure provides compounds having formula (I):

(I)

or a pharmaceutically acceptable salt or solvate thereof, wherein:

X is CH$_2$, O, NH or N(C$_1$-C$_6$)alkyl;

Y and Z form CONH or CH$_2$O;

R$^1$ and R$^2$ are each independently hydrogen, a side chain of a natural amino acid, a linear, branched or cyclic alkyl, a linear, branched or cyclic alkenyl, a linear, branched or cyclic alkynyl, or substituted or unsubstituted aryl;

R$^3$ is hydrogen or (C$_1$-C$_6$)alkyl;

the Activated Carbonyl Group is and

R$^4$ is a linear, branched or cyclic alkyl, a linear, branched or cyclic alkenyl, a linear, branched or cyclic alkynyl, or substituted or unsubstituted aryl.

In another aspect the disclosure provides compounds having formula (I), wherein X is NH; R$^1$, R$^2$, and R$^3$ are each independently hydrogen, CH$_3$, CH$_2$CH$_3$, (CH$_2$)$_2$CH$_3$, CH(CH$_3$)$_2$, (CH$_2$)$_3$CH$_3$, CH$_2$CH(CH$_3$)$_2$, or —C(CH$_3$)$_3$; and R$^4$ is (CH$_2$)$_{13}$CH$_3$.

In another aspect the disclosure provides compounds having formula (I), wherein the compound of formula (I) has structure:

In another aspect the disclosure provides a pharmaceutical composition for use in inhibiting the enzymatic activity of phospholipase A$_2$ in a cell or organism, comprising a pharmaceutically acceptable carrier and a compound of formula (I).

In another aspect the disclosure provides a pharmaceutical composition for use in inhibiting the enzymatic activity of phospholipase A$_2$ in a cell or organism, comprising a pharmaceutically acceptable carrier and a compound of formula (I), wherein the enzymatic activity inhibited is of phospholipase cPLA$_2$, iPLA$_2$ or sPLA$_2$.

In another aspect the disclosure provides a pharmaceutical composition for use in inhibiting the enzymatic activity of phospholipase A$_2$ in a cell or organism, comprising a pharmaceutically acceptable carrier and a compound of formula (I), wherein the enzymatic activity inhibited is of phospholipase cPLA$_2$, iPLA$_2$ or sPLA$_2$, wherein the compound of formula (I) has structure:

In another aspect, the disclosure provides a pharmaceutical composition for use in inhibiting the enzymatic activity of iPLA$_2$ in a cell or organism, comprising a pharmaceutically acceptable carrier and a compound of formula (I).

In another aspect, the disclosure provides a pharmaceutical composition for use in inhibiting the enzymatic activity of cPLA$_2$ in a cell or organism, comprising a pharmaceutically acceptable carrier and a compound of formula (I).

In another aspect, the disclosure provides a pharmaceutical composition for use in inhibiting the enzymatic activity of cPLA$_2$ in a cell or organism and inhibiting the cellular release of arachidonic acid, comprising a pharmaceutically acceptable carrier and a compound of formula (I).

In another aspect, the disclosure provides a method for modulating the effects of inflammatory processes in a mammal, comprising administering an effective amount of the compound of formula (I).

In another aspect, the disclosure provides a method for modulating the effects of inflammatory processes in a mammal, comprising administering an effective amount of the compound of formula (I), wherein the mammal is a human.

DETAILED DESCRIPTION OF THE DISCLOSURE

The contents of co-pending, co-owned U.S. Utility patent application Ser. No. 10/506,059, filed on Mar. 7, 2003, and Ser. No. 12/064,013, filed Aug. 17, 2006 are hereby incorporated by reference for all purposes.

All patents and other references cited in the specification are indicative of the level of skill of those skilled in the art to which the disclosure pertains, and are incorporated by reference in their entireties, including any tables and figures, to the same extent as if each reference had been incorporated by reference in its entirety individually.

One skilled in the art would readily appreciate that the present disclosure is well adapted to obtain the ends and advantages mentioned, as well as those inherent therein. The methods, variances, and compositions described herein as presently representative of preferred embodiments are exemplary and are not intended as limitations on the scope of the disclosure. Changes therein and other uses will occur to those skilled in the art, which are encompassed within the spirit of the disclosure, are defined by the scope of the claims.

Definitions provided herein are not intended to be limiting from the meaning commonly understood by one of skill in the art unless indicated otherwise.

Design of Inhibitors

Figure 1:
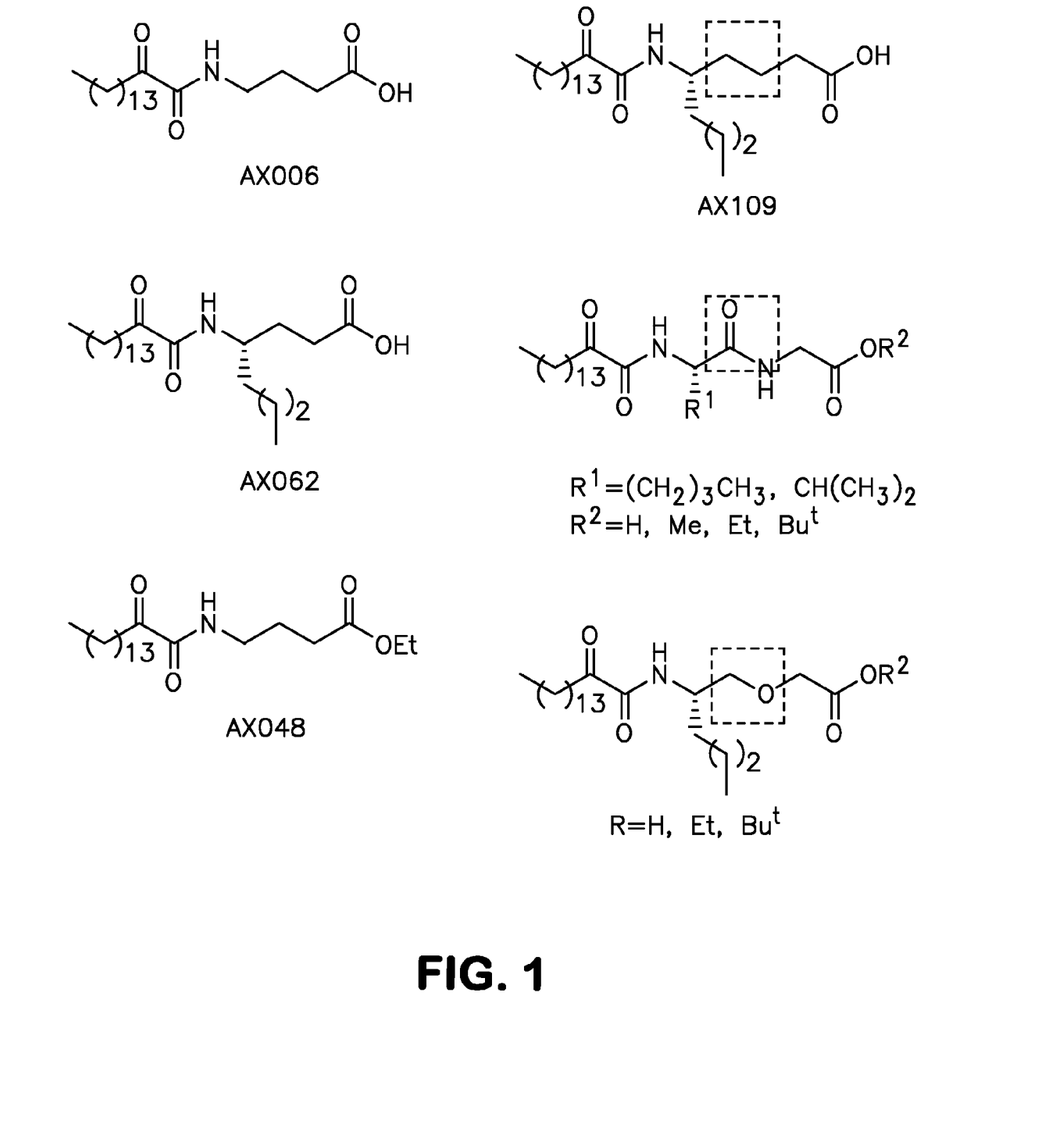
FIG. 1 shows 2-oxoamide inhibitors.
Figure 2:
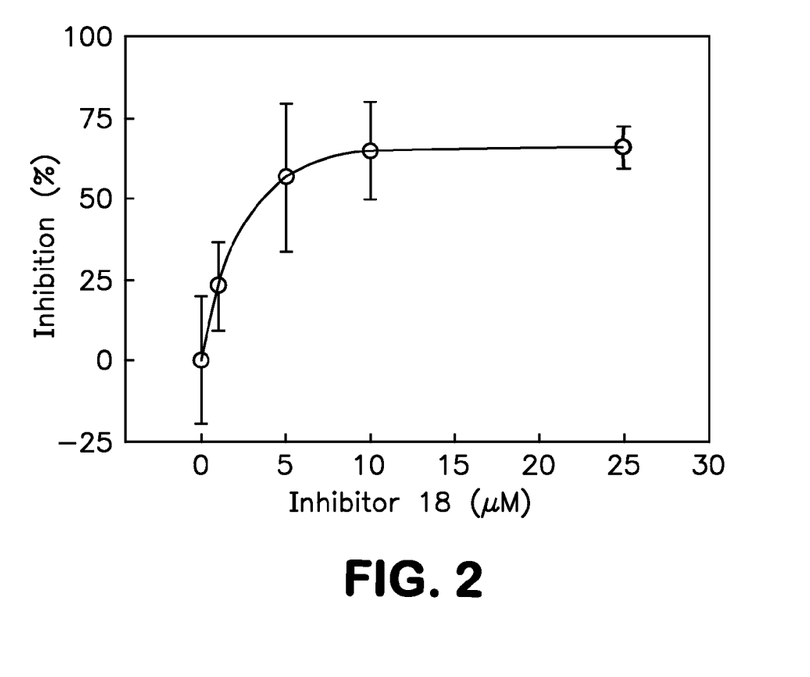
FIG. 2 illustrates the dose response curve for the inhibition of AA release from RAW 264.7 cells by inhibitor 18. RAW 264.7 cells were preincubated with the indicated concentrations of 18 prior to stimulation with Kdo$_2$-Lipid A and AA quantitation. The data is graphically expressed in terms of percent inhibition of AA release as a function of the concentration of 18. The curve is a fit of the data to a nonlinear regression function using the Sigma Plot program. Based on the maximal inhibition observed in this assay, half maximal inhibition occurs at about 2 μM of 18.
Figure 3:
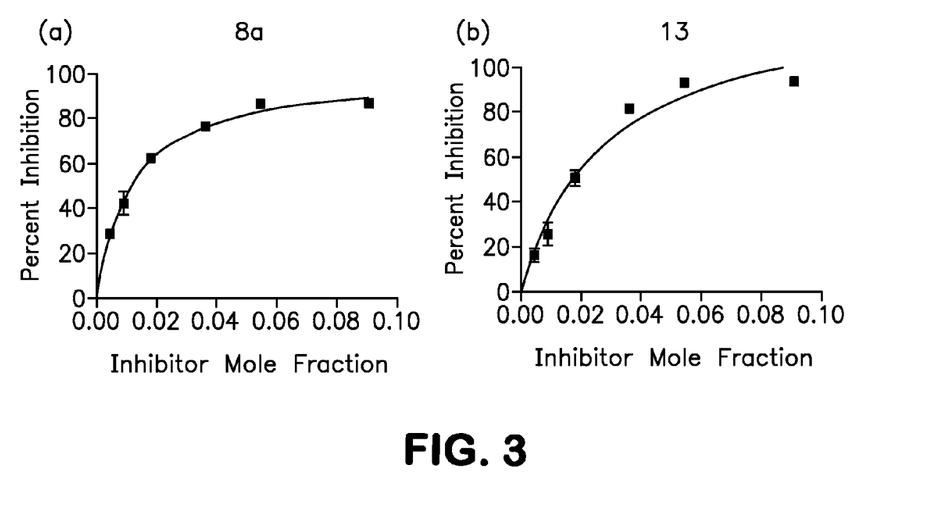
FIG. 3 illustrates the dose-response curves for 2-oxoamide inhibitors of GVIA iPLA$_2$. Inhibition of the activity of human GVIA iPLA$_2$ by inhibitors (a) 8a and (b) 13 was tested on mixed-micelles containing 100 μM PAPC and 400 μM Triton X-100. Inhibition curves were generated by Graphpad Prism using a non-linear regression (one-site binding model—hyperbola) to calculate the reported X$_I$(50) values.

Dipeptides are considered to be δ-amino acid analogues, because of the distance between the N- and C-terminal groups (FIG. 1). Ether pseudopeptide derivatives may be also considered δ-amino acid derivatives. Thus, the present disclosure uses L-norleucine and L-valine as starting materials to synthesize a series of derivatives that contain the 2-oxoamide functionality and an amide group or ether group to replace the two methylenes of the δ-amino acid derivative. The replacement of the peptide bond with a suitable surrogate can increase the stability of peptides toward enzymatic hydrolysis, prolong the half-time of peptide action and improve the transport of peptides into cells. In addition, using amide bond isosters is a convenient way to elucidate the role of the amide unit in protein-ligand interactions and thus, to understand the structure-biological activity relationship. The methylene ether group constitutes an interesting amide bond surrogate, since the calculated $C_\alpha^i$-$C_\alpha^{i+1}$ distance of $\psi[CH_2O]$ pseudodipeptides (3.7 Å) is almost the same as that in a dipeptide (3.8 Å). In the past, ether pseudopeptides have been studied such as renin and cAMP-dependent protein kinase inhibitors, as agonists of substance P, and as analogues of the antidiuretic drug desmopressin.

Synthesis of Inhibitors

Scheme 1 outlines the synthesis of compounds 4a-c. N-Protected L-norleucine (1a) and L-valine (1b) were coupled with methyl and ethyl glycinate using 1-(3-dimethylaminopropyl)-3-ethyl carbodiimide (WSCI) as a condensing agent in the presence of 1-hydroxybenzotriazole (HOBt). Removal of the Boc group, followed by coupling with 2-hydroxyhexadecanoic acid yielded 2-hydroxyamides 3a-c, which were oxidized either by the Dess-Martin method or by the NaOCl/AcNH-TEMPO method to the target compounds 4a-c.

Scheme 1

| 1-3 | R¹ | R² |
|---|---|---|
| a | n-Bu | Me |
| b | i-Pr | Me |
| c | n-Bu | Et |

Reagents and conditions: (a) HCl.H-Gly-OR², Et₃N, WSCI, HOBt, CH₂Cl₂; (b) 4N HCl/Et₂O; (c) CH₃(CH₂)₁₃CHOHCOOH, Et₃N, WSCI, HOBt, CH₂Cl₂; (d) Dess-Martin reagent, CH₂Cl₂; (e) NaOCl, AcNH-TEMPO, NaBr, NaHCO₃, EtOAc/PhCH₃/H₂O 3:3:0.5, 0° C.

Scheme 2 outlines the synthesis of compounds 9a,b. Following similar reactions, tent-butyl ester derivatives 8a,b were prepared as depicted in Scheme 2. Starting from Z-protected norleucine and valine. 2-Oxoamides 9a,b, containing a free carboxyl group, were obtained by treatment of 8a,b with trifluoroacetic acid.

Scheme 2

| 5-9 | R |
|---|---|
| a | n-Bu |
| b | i-Pr |

Reagents and conditions: (a) HCl.H-Gly-OBuᵗ, Et₃N, WSCI, HOBt, CH₂Cl₂; (b) H₂, 10% Pd/C, EtOH; (c) CH₃(CH₂)₁₃CHOHCOOH, Et₃N, WSCI, HOBt, CH₂Cl₂; (d) Dess-Martin reagent, CH₂Cl₂; (e) NaOCl, AcNH-TEMPO, NaBr, NaHCO₃, EtOAc/PhCH₃/H₂O 3:3:0.5, 0° C.; (f) 50% TFA/CH₂Cl₂.

The synthesis of pseudopeptide derivatives is described in Schemes 3 and 4. Scheme 3 outlines the synthesis of Boc-L-norleucinol (10), obtained by reduction of Boc-L-norleucine, reacted with ethyl bromoacetate using sodium hydride in the presence of 18-crown-6 to produce ether 11. Removal of Boc group, followed by coupling and oxidation yielded 2-oxoamide 13.

Scheme 3.

Reagents and conditions: (a) BrCH₂COOEt, NaH, 18-crown-6, THF; (b) 4N HCl/Et₂O; (c) CH₃(CH₂)₁₃CHOHCOOH, Et₃N, WSCI, HOBt, CH₂Cl₂; (d) Dess-Martin reagent, CH₂Cl₂.

Scheme 4 outlines the synthesis of pseudodipeptide derivatives 17 and 18 prepared by similar procedures. However, for the synthesis of tert-butyl ester derivative the reaction of Z-L-norleucinol with tert-butyl bromoacetate was carried out under phase transfer conditions.

Scheme 4

-continued

Reagents and conditions: (a) BrCH$_2$COOBu$^t$, Bu$_4$NHSO$_4$, 50% NaOH, C$_6$H$_6$; (b) H$_2$, 10% Pd/C, EtOH; (c) CH$_3$(CH$_2$)$_{13}$CHOHCOOH, Et$_3$N, WSCI, HOBt, CH$_2$Cl$_2$; (d) Dess-Martin reagent, CH$_2$Cl$_2$; (e) 50% TFA/CH$_2$Cl$_2$.

In Vitro Inhibition of GIVA cPLA$_2$, GVIA iPLA$_2$ and GV sPLA$_2$

All the inhibitors synthesized in this work were tested for inhibition of GIVA cPLA$_2$, GVIA iPLA$_2$ and GV sPLA$_2$ using mixed micellar assays. Details for the assays have been published previously. The results of the inhibition are presented in Table 1 using either percent inhibition or X$_I$(50) values. Initially, the percent inhibition of each PLA$_2$ at 0.091 mole fraction of inhibitor was determined. X$_I$(50) values were estimated when the percent inhibition was higher than 90%. The X$_I$(50) is the mole fraction of the inhibitor in the total substrate interface required to inhibit the enzyme by 50%. Data for the reference 2-oxoamide inhibitors AX006 and AX048 are included in Table 1 for comparison.

Dipeptide-based 2-oxoamides 9a and 9b containing a free carboxyl group inhibited GIVA cPLA$_2$ without affecting the activity of the other intracellular enzyme GVIA iPLA$_2$. This observation is in full agreement with our previous report, that amino acid-based 2-oxoamides containing a free carboxyl group are selective inhibitors of GIVA cPLA$_2$.

Methyl ester 4a based on dipeptide Nle-Gly and tert-butyl ester 8b based on dipeptide Val-Gly, inhibited both GIVA cPLA$_2$ and GVIA iPLA$_2$, showing a small preference for GIVA cPLA$_2$. The methyl ester 4b based on dipeptide Val-Gly lost the activity against both GIVA cPLA$_2$ and GVIA iPLA$_2$. To the contrary, the tert-butyl ester 8a and the ethyl ester 4c, both based on Nle-Gly dipeptide presented potent inhibition of GVIA iPLA$_2$ with X$_I$(50) values of 0.011 and 0.020, respectively. At the same time, both 8a and 4c inhibited very weakly GIVA cPLA$_2$ and GV sPLA$_2$.

A bioisosteric replacement of the amide bond in compounds 4c, 8a and 9a by an ether group, resulted to the structurally related compounds 13, 17 and 18. Pseudodipeptide derivative 18, selectively inhibited GIVA cPLA$_2$, as expected, due to the free carboxyl group. This derivative is the most potent inhibitor of GIVA cPLA$_2$ [X$_I$(50) 0.017] identified in the present work and its potency is comparable to that of the reference 2-oxoamide inhibitor AX006 [X$_I$(50) 0.024].[15] Interestingly, both ethyl ester 13 and tert-butyl ester 17 preferentially inhibited GVIA iPLA$_2$. In particular, derivative 13 is a potent inhibitor of GVIA iPLA$_2$ with a X$_I$(50) value of 0.017, while high mole fraction (0.091) of the inhibitor caused only 52% inhibition of GIVA cPLA$_2$.

Among the compounds tested in this study, only two esters (compounds 8b and 13) were able to reduce GV sPLA$_2$ activity (around 80% inhibition at 0.091 mole fraction). GV sPLA$_2$ utilizes a catalytic histidine to activate a water molecule as the nucleophile in phospholipid hydrolysis. Although there is no serine nucleophile in GV sPLA$_2$, the 2-oxoamides may resemble the substrate phospholipids or the transition state such that they would bind to the GV sPLA$_2$ active site and inhibit the enzyme.

Both the intracellular enzymes GIVA cPLA$_2$ and GVIA iPLA$_2$ share the same catalytic mechanism using active site serine as the nucleophilic residue. Thus, compounds designed to inhibit GIVA cPLA$_2$, may show cross reactivity with GVIA iPLA$_2$. Very interestingly, ethyl and tert-butyl esters 4c, 8a, 13 and 17, based on Nle-Gly or the corresponding ether pseudodipeptide preferentially inhibit GVIA iPLA$_2$. Up to now, it has been shown that 2-oxoamide esters may inhibit both GIVA cPLA$_2$ and GVIA iPLA$_2$ either with similar potency or with a preference for GIVA cPLA$_2$. However, identified for the first time in the course of the present work are several 2-oxoamides, such as 8a or 13, which show higher inhibition against GVIA iPLA$_2$ than GIVA cPLA$_2$. It seems that the replacement of the amino acid unit of a 2-oxoamide inhibitor by a dipeptide unit may shift the selectivity in favour of GVIA iPLA$_2$. Since there is a lack of potent and selective inhibitors for GVIA iPLA$_2$, the findings of the present study will help in designing 2-oxoamides presenting selectivity for this particular PLA$_2$.

Ex Vivo Inhibition of Cellular Arachidonic Aid Release

Arachidonic acid (AA) is the ideal metabolic indicator of GIVA cPLA$_2$ activity, since it is the product of GIVA cPLA$_2$-mediated catalysis. In addition to some of the new 2-oxoamides based on dipeptides and pseudodipeptides that were synthesized in this work, a series of potent 2-oxoamide in vitro inhibitors of GIVA cPLA$_2$, previously reported by us, were further tested in a cellular ex vivo system to investigate whether they reduced cellular AA production. For this purpose, RAW 264.7 macrophages were preincubated with 25 μM concentrations of the inhibitor prior to treatment of the cells with Kdo$_2$-Lipid A. Subsequently, AA release was quantitated from the supernatants.

The results of our studies for twenty one 2-oxoamides are summarized in Table 2. Note that some of the compounds led to an actual increase or activation of AA release which is not unusual in this kind of assay due to detergent or other non-specific effects. Those compounds giving an activation of AA release were not evaluated further. Compounds 18, 19, 20 25, 26, 30 and 35, which contain a free carboxyl group and are potent and selective inhibitors of GIVA cPLA$_2$, induce a significant reduction of AA release. Derivatives 26 and 30, based on γ-norleucine, cause the highest inhibition percentage in AA release. Both strongly inhibit GIVA cPLA$_2$. Comparison between compounds 20 and 26 indicates the importance of the long aliphatic chain. Compound 19, based on γ-aminobutyric acid and compound 25, based on γ-leucine, cause significant inhibition, though to a lesser extent, of AA production. Moderate inhibitors of GIVA cPLA$_2$ result to a lower inhibition of AA release (compounds 21, 28). Compound 35, a δ-norleucine derivative, and compound 18, based on an pseudodipeptide, which also can be considered as a δ-amino acid analogue, lead to a considerable AA reduction in cells. Both molecules are strong inhibitors of GIVA cPLA$_2$.

Although production of arachidonic acid can be catalyzed by other phospholipases as well, such as GVIA iPLA$_2$ and GV sPLA$_2$, most of the non-selective inhibitors of the three phospholipases tested here, did not show a significant inhibitory effect on AA release. Compounds 23, 24, 27, 29, 31 and 36 carry an esterified carboxyl group. In compound 32, the ester group has been replaced by a sulfonamide group. They all inhibit GIVA cPLA$_2$ to a high extent, though not selectively, since they inhibit also both GVIA iPLA$_2$ and GV sPLA$_2$.

Dipeptide inhibitor 8b reduced the cellular release of AA by 30%, while derivative 18 reduced AA production by 68%. Interestingly, the 2-oxoamide inhibitor 18, which contains a free carboxyl group, leads to more than double the AA release inhibition, indicating the importance of selectivity of an inhibitor against GIVA cPLA$_2$.

IC$_{50}$ Values for Arachidonic Acid Inhibition

Dose response curves were measured for the seven synthetic inhibitors that reduced AA release the most (see Table 2) in order to calculate the IC$_{50}$ values. All of these contained free carboxylic acids and were specific for GIVA cPLA$_2$. The IC$_{50}$ values for these seven compounds are summarized in Table 3. The individual dose response curve for the inhibition of AA release from RAW 264.7 cells stimulated with Kdo$_2$-Lipid A in the presence of 18 is depicted in FIG. 1. Inhibitors 19, 25, 26 and 30 all display IC$_{50}$ values of approximately 25 uM whereas 20, 35 and 18 display values of 10, 7 and 2 uM, respectively. Interestingly, inhibitors 35 and 18, which contain the carboxylic acid functional group spaced at the 5 position relative to the 2-oxoamide moiety, demonstrated the lowest IC$_{50}$ values at 7 and 2 uM, respectively. In contrast, the five γ linked inhibitors, 19, 20, 25, 26 and 30, all displayed higher IC$_{50}$ values at 25, 10, 25, 25 and 25 uM. These data suggest that inhibitors with 5 structural spacing display more effective AA release inhibition than γ structural spacing within this inflammatory cellular model. Of course, this specificity may relate to the ability of the compound to be taken up by the cell and other factors, but these results demonstrate that the oxoamides are able to inhibit within the cellular milieu.

The disclosure provides new 2-oxoamides based on dipeptides and pseudodipeptides. These compounds containing a free carboxyl group are selective GIVA cPLA$_2$ inhibitors and also preferentially inhibit AA release intracellularly. 2-Oxoamides ethyl and tert-butyl esters, based on the dipeptide Nle-Gly or the corresponding ether pseudodipeptide, preferentially inhibit the other major intracellular enzyme GVIA iPLA$_2$. The disclosed compounds are potent inhibitors of GVIA iPLA$_2$ with X$_I$(50) values between 0.011-0.020. These results also demonstrate that selective GIVA cPLA$_2$ inhibitors inhibit AA release in RAW 264.7 macrophages, and 2-oxoamide compounds based on a pseudodipeptide inhibits AA release with an IC$_{50}$ value of 2 μM.

EXAMPLES

Melting points were determined on a Buchi 530 apparatus and are uncorrected. Specific rotations were measured at 25° C. on a Perkin-Elmer 343 polarimeter using a 10 cm cell. NMR spectra were recorded on a Varian Mercury (200 MHz) spectrometer. All amino acid derivatives were purchased from Fluka Chemical Co. Electron spray ionization (ESI) mass spectra were recorded on a Finnigan, Surveyor MSQ Plus spectrometer. TLC plates (silica gel 60 F254) and silica gel 60 (70-230 or 230-400 mesh) for column chromatography were purchased from Merck. Visualization of spots was effected with UV light and/or phosphomolybdic acid and/or ninhydrin, both in ethanol stain. Tetrahydrofuran was dried by standard procedures and stored over molecular sieves or Na. All other solvents and chemicals were reagent grade and used without further purification. Inhibitors 25 and 26 were prepared according to procedures described in the literature.

Synthesis of 2-Oxoamide Inhibitors

Example 1

General Method for the Coupling of 2-hydroxy-hexadecanoic Acid with Amino Components To a stirred solution of 2-hydroxy-hexadecanoic acid (0.27 g, 1.0 mmol) and hydrochloride amino component (1.0 mmol) in dichloromethane (10 mL), triethylamine (0.3 mL, 2.2 mmol) and subsequently 1-(3-dimethylaminopropyl)-3-ethyl carbodiimide hydrochloride (WSCI) (0.21 g, 1.1 mmol) and 1-hydroxybenzaniazole (HOBt) (0.14 g, 1.0 mmol) were added at 0° C. The reaction mixture was stirred for 1 h at 0° C. and overnight at room temperature. The solvent was evaporated under reduced pressure and ethyl acetate (20 mL) was added. The organic layer was washed consecutively with brine, 1N HCl, brine, 5% NaHCO$_3$, and brine, dried over Na$_2$SO$_4$ and evaporated under reduced pressure. The residue was purified by column-chromatography using CHCl$_3$—CHCl$_3$/MeOH 99:1 as eluent.

Example 2

Methyl 2-((S)-2-(2-hydroxyhexadecanamido)hexanamido)acetate (Mixture of Diastereomers) (3a)

Yield 68%; White solid; mp 78-80° C.; $^1$H NMR (200 MHz, CDCl$_3$) δ 7.53-7.45 (m, 1H), 7.40 (d, J=8.6 Hz, 1H), 4.59-4.43 (m, 1H), 4.15-4.06 (m, 1H), 4.02-3.94 (m, 2H), 3.71 (s, 3H), 1.89-1.53 (m, 4H), 1.23 (br s, 28H), 0.98-0.80 (m, 6H); $^{13}$C NMR (50 MHz, CDCl$_3$) δ 175.1 (174.8), 172.7 (172.5), 170.1 (170.0), 72.0 (71.9), 52.4 (52.7), 52.2, 41.1, 34.8 (34.6), 32.0 (31.8), 29.6, 29.5, 29.3, 27.6, 27.5, 25.0, 22.6, 22.3, 22.2, 14.0, 13.8. Anal. Calcd for C$_{25}$H$_{48}$N$_2$O$_5$: C, 65.75; H, 10.59; N, 6.13. Found: C, 65.49; H, 10.78; N, 6.01.

Example 3

Methyl 2-((S)-2-(2-hydroxyhexadecanamido)-3-methylbutanamido)-acetate (Mixture of Diastereomers) (3b)

Yield 73%; mp 109-111° C.; $^1$H NMR (200 MHz, CDCl$_3$) δ 7.34-7.15 (m, 2H), 4.43-4.27 (m, 1H), 4.10-3.96 (m, 3H), 3.75 (s, 3H), 2.24-2.08 (m, 1H), 1.87-1.63 (m, 2H), 1.26 (br s, 24H), 1.05-0.91 (m, 6H), 0.88 (t, J=6.6 Hz, 3H). Anal. Calcd for C$_{24}$H$_{46}$N$_2$O$_5$: C, 65.12; H, 10.47; N, 6.33. Found: C, 64.98; H, 10.68; N, 6.18.

Example 4

Ethyl 2-((S)-2-(2-hydroxyhexadecanamido)hexanamido)acetate (Mixture of Diastereomers) (3c)

Yield 64%; White solid; mp 77-79° C.; $^1$H NMR (200 MHz, CDCl$_3$) δ 7.31-7.07 (m, 2H), 4.59-4.42 (m, 1H), 4.25-4.06 (m, 3H), 4.02-3.95 (m, 2H), 1.97-1.51 (m, 4H), 1.24 (br s, 31H), 0.97-0.80 (m, 6H); $^{13}$C NMR (50 MHz, CDCl$_3$) δ 174.9 (174.5), 172.4 (172.1), 169.7 (169.5), 72.1 (72.0), 61.5, 52.5 (52.7), 41.3, 34.6 (34.8), 31.9, 29.7, 29.4, 29.3, 27.6, 25.0, 22.7, 22.3, 14.1, 13.9. Anal. Calcd for C$_{26}$H$_{50}$N$_2$O$_5$: C, 66.35; H, 10.71; N, 5.95. Found: C, 66.19; H, 10.99; N, 5.89.

Example 5 tert-Butyl 2-((S)-2-(2-hydroxyhexadecanamido)hexanamido)acetate (Mixture of Diastereomers) (7a)

Yield 69%; White solid; mp 50-52° C.; $^1$H NMR (200 MHz, CDCl$_3$) δ 7.37-7.26 (m, 1H), 7.23-7.08 (m, 1H), 4.58-4.45 (m, 1H), 4.15-4.03 (m, 1H), 3.97-3.81 (m, 2H), 1.98-1.52 (m, 4H), 1.44 (s, 9H), 1.24 (br s, 28H), 0.98-0.79 (m, 6H); $^{13}$C NMR (50 MHz, CDCl$_3$) δ 174.9 (174.6), 172.4 (172.1), 168.6 (168.7), 82.2, 72.1 (72.0), 52.9 (52.5), 42.0, 34.8 (34.6), 32.1, 31.8, 29.6, 29.5, 29.3, 27.9, 27.6, 27.5, 25.0, 22.6, 22.3, 22.2, 14.0, 13.8. Anal. Calcd for C$_{28}$H$_{54}$N$_2$O$_5$: C, 67.43; H, 10.91; N, 5.62. Found: C, 67.28; H, 11.08; N, 5.47.

Example 6 tert-Butyl 2-((S)-2-(2-hydroxyhexadecanamido)-3-methylbutan-amido)acetate (Mixture of Diastereomers)(7b)

Yield 81%; White solid; mp 81-83° C.; $^1$H NMR (200 MHz, CDCl$_3$) δ 7.25 (d, J=8.8 Hz, ½H), 7.16 (d, J=8.8 Hz, ½H), 6.96 (t, J=4.8 Hz, ½H), 6.88 (t, J=4.8 Hz, ½H), 4.34-4.22 (m, 1H), 4.18-4.03 (m, 1H), 3.92-3.81 (m, 2H), 2.23-2.05 (m, 1H), 1.84-1.48 (m, 2H), 1.42 (s, 9H), 1.21 (br s, 24H), 0.93 (t, J=5.8 Hz, 6H), 0.84 (t, J=6.6 Hz, 3H); $^{13}$C (50 MHz, CDCl$_3$) $^{13}$C NMR δ 174.7 (175.0), 171.7 (171.4), 168.8 (168.6), 82.4, 72.3 (72.0), 58.1 (57.9), 42.0, 34.9 (34.6), 31.9, 30.8 (30.7), 29.7, 29.6, 29.4, 29.3, 28.0, 25.0, 22.6, 19.3, 18.1, 14.1. Anal. Calcd for C$_{27}$H$_{52}$N$_2$O$_5$: C, 66.90; H, 10.81; N, 5.78. Found: C, 66.65; H, 10.98; H, 5.62.

Example 7

Ethyl 2-((S)-2-(2-hydroxyhexadecanamido)hexyloxy)acetate (Mixture of Diastereomers) (12)

Yield 69%; Waxy white solid; $^1$H NMR (200 MHz, CDCl$_3$) δ 7.03-6.92 (m, 1H), 4.25-3.95 (m, 6H), 3.65-3.42 (m, 2H), 1.83-1.53 (m, 4H), 1.25 (br s, 31H), 0.95-1.79 (m, 6H); $^{13}$C NMR (50 MHz, CDCl$_3$) δ 174.2 (173.9), 170.8 (170.7), 73.2 (73.1), 72.2 (71.8), 68.0 (68.1), 61.0, 48.5 (48.8), 34.9 (34.7), 31.8, 31.0, 29.6, 29.5, 29.4, 29.3, 28.1, 24.9, 24.8, 22.6, 22.5, 14.0, 13.9. Anal. Calcd for C$_{26}$H$_{51}$NO$_5$: C, 68.23; H, 11.23; N, 3.06. Found: C, 68.04; H, 11.34; N, 2.91.

Example 8 tert-Butyl 2-((S)-2-(2-hydroxyhexadecanamido)hexyloxy)acetate (Mixture of Diastereomers) (16)

Yield 77%; Oil; $^1$H NMR (200 MHz, CDCl$_3$) δ 7.05 (d, J=8.8 Hz, 1H), 4.17-3.96 (m, 2H), 3.93 (s, 2H), 3.73 (br s, 1H), 3.57 (dd, J$_1$=9.6 Hz, J$_2$=3.6 Hz, 1H), 3.45 (dd, J$_1$=8.8 Hz, J$_2$=3.6 Hz, 1H), 1.90-1.55 (m, 4H), 1.45 (s, 9H), 1.23 (br s, 28H), 0.98-1.78 (m, 6H); $^{13}$C NMR (50 MHz, CDCl$_3$) δ 174.2 (174.0), 170.1, 82.0, 73.2, 72.2 (71.7), 68.4 (68.6), 48.7 (48.9), 34.7 (35.0), 31.9, 31.0, 29.6, 29.5, 29.3, 28.2, 28.0, 24.9, 24.8, 22.6, 22.5, 14.0, 13.9. Anal. Calcd for C$_{28}$H$_{55}$NO$_5$: C, 69.23; H, 11.41; N, 2.88. Found: C, 69.01; H, 11.59; N, 2.73.

Example 9

General Method for the Oxidation of 2-hydroxy-amides: Method A

To a solution of 2-hydroxy-amide (1 mmol) in dry dichloromethane (10 mL) Dess-Martin periodinane was added (0.64 gr, 1.5 mmol) and the mixture was stirred for 1 h at room temperature. The organic solution was washed with 10% aqueous NaHCO$_3$, dried over Na$_2$SO$_4$ and the organic solvent was evaporated under reduced pressure. The residue was purified by column-chromatography using chloroform as eluent.

Example 10

(S)-Methyl 2-(2-(2-oxohexadecanamido)hexanamido)acetate (4a)

Yield 85%; White solid; mp 65-67° C.; [α]$_D$=−21.8 (c 0.5 CHCl$_3$); $^1$H NMR (200 MHz, CDCl$_3$) δ 7.50 (d, J=8.4 Hz, 1H), 6.74 (t, J=5.4 Hz, 1H), 4.49-4.37 (m, 1H), 4.17-3.95 (m, 2H), 3.75 (s, 3H), 2.89 (t, J=7.6 Hz, 2H), 2.05-1.47 (m, 4H), 1.24 (br s, 26H), 0.97-0.81 (m, 6H); $^{13}$C NMR (50 MHz, CDCl$_3$) δ 198.3, 170.9, 170.0, 160.0, 53.0, 52.4, 41.1, 36.8, 31.9, 31.8, 29.6, 29.5, 29.4, 29.3, 29.0, 27.4, 23.0, 22.6, 22.3, 14.1, 13.8; MS (ESI): m/z (%): 477 (77) [M+Na]$^+$; Anal. Calcd for C$_{25}$H$_{46}$N$_2$O$_5$: C, 66.04; H, 10.20; N, 6.16. Found: C, 66.19; H, 10.13; N, 6.21.

Example 11

(S)-Ethyl 2-(2-(2-oxohexadecanamido)hexanamido) acetate (4c)

Yield 76%; White solid; mp 63-65° C.; [α]$_D$=−20.8 (c 0.5 CHCl$_3$); $^1$H NMR (200 MHz, CDCl$_3$) δ 7.51 (d, J=8.4 Hz, 1H), 6.76 (t, J=5.2, 1H), 4.50-4.36 (m, 1H), 4.19 (q, J=7 Hz, 2H), 4.12-3.91 (m, 2H), 2.88 (t, J=7.4 Hz, 2H), 2.05-1.45 (m, 4H), 1.26 (br s, 29H), 0.95-0.80 (m, 6H); $^{13}$C NMR (50 MHz, CDCl$_3$) δ 198.3, 170.9, 169.5, 160.1, 61.6, 53.0, 41.3, 36.8, 32.0, 31.9, 29.6, 29.5, 29.4, 29.3, 29.0, 27.5, 23.0, 22.6, 22.3, 14.1, 13.8; MS (ESI): m/z (%): 491 (100) [M+Na]$^+$, 469 (55) [M+]$^+$; Anal. Calcd for C$_{26}$H$_{48}$N$_2$O$_5$: C, 66.63; H, 10.32; N, 5.98. Found: C, 66.58; H, 10.39; N, 5.91.

Example 12

(S)-tert-Butyl 2-(2-(2-oxohexadecanamido)hexanamido)acetate (8a)

Yield 85%; White solid; mp 38-39° C.; [α]$_D$=−17.2 (c 0.5 CHCl$_3$); $^1$H NMR (200 MHz, CDCl$_3$) δ 7.47 (d, J=8.4 Hz, 1H), 6.57 (t, J=5 Hz, 1H), 4.48-4.35 (m, 1H), 4.03-3.80 (m, 2H), 2.89 (t, J=8 Hz, 2H), 2.02-1.52 (m, 4H), 1.45 (s, 9H), 1.24 (br s, 26H), 0.97-0.79 (m, 6H); $^{13}$C NMR (50 MHz, CDCl$_3$) δ 198.3, 170.7, 168.5, 160.1, 82.4, 53.1, 42.0, 36.8, 32.0, 31.9, 29.6, 29.5, 29.4, 29.3, 29.0, 28.0, 27.5, 23.1, 22.6, 22.3, 14.1, 13.8; MS (ESI): m/z (%): 519 (100) [M+Na]$^+$, 497 (32) [M+H]$^+$; Anal. Calcd for C$_{28}$H$_{52}$N$_2$O$_5$: C, 67.70; H, 10.55; N, 5.64. Found: C, 67.58; H, 10.73; N, 5.58.

Example 13

(S)-Ethyl 2-(2-(2-oxohexadecanamido)hexyloxy) acetate (13)

Yield 88%; White solid; mp 41-43° C.; $[\alpha]_D$=−8.4 (c 0.5 CHCl$_3$); $^1$H NMR (200 MHz, CDCl$_3$) δ 7.29 (d, J=9.6 Hz, 1H), 4.21 (q, J=7.4 Hz, 2H), 4.06 (s, 2H), 4.05-3.91 (m, 1H), 3.64 (dd, J$_1$=9.6 Hz, J$_2$=4.0 Hz, 1H), 3.52 (dd, J$_1$=9.4 Hz, J$_2$=3.8 Hz, 1H), 2.90 (t, J=6.6 Hz, 2H), 1.71-1.48 (m, 4H), 1.24 (br s, 29H), 0.96-0.80 (m, 6H); $^{13}$C NMR (50 MHz, CDCl$_3$) δ 199.2, 170.3, 159.9, 72.5, 68.2, 60.9, 49.4, 36.8, 31.9, 30.9, 29.6, 29.5, 29.4, 29.3, 29.0, 28.0, 23.1, 22.6, 22.4, 14.1, 13.9; MS (ESI): m/z (%): 478 (100) [M+Na]$^+$; Anal. Calcd for C$_{26}$H$_{49}$NO$_5$: C, 68.53; H, 10.84; N, 3.07. Found: C, 68.65; H, 10.71; N, 3.12.

Example 14

(S)-tert-Butyl 2-(2-(2-oxohexadecanamido)hexyloxy)acetate (17)

Yield 93%; white solid; Low mp; $[\alpha]_D$=−10.8 (c 0.5 CHCl$_3$); $^1$H NMR (200 MHz, CDCl$_3$) δ 7.26 (d, J=8.8 Hz, 1H), 4.03-3.85 (m, 3H), 3.61 (dd, J$_1$=9.4 Hz, J$_2$=4.0 Hz, 1H), 3.49 (dd, J$_1$=9.4 Hz, J$_2$=4.0 Hz, 1H), 2.89 (t, J=7.2 Hz, 2H), 1.69-1.48 (m, 4H), 1.45 (s, 9H), 1.23 (br s, 26H), 0.96-0.79 (m, 6H); $^{13}$C NMR (50 MHz, CDCl$_3$) δ 199.2, 169.4, 160.0, 81.7, 72.4, 68.7, 49.4, 36.7, 31.8, 31.0, 29.6, 29.5, 29.4, 29.3, 29.0, 28.0, 23.1, 22.6, 22.4, 14.0, 13.9; MS (ESI): (%): 506 (57) [M+Na]$^+$; Anal. Calcd for C$_{28}$H$_{53}$NO$_5$: C, 69.52; H, 11.04; N, 2.90. Found: C, 69.57; H, 11.08; N, 2.83.

Example 15

General Method for the Oxidation of 2-hydroxy-amides. Method B

To a solution of 2-hydroxy-amide (1.0 mmol) in a mixture of toluene (3 mL) and ethyl acetate (3 mL) a solution of NaBr (0.11 g, 1.1 mmol) in water (0.5 mL) was added followed by AcNH-TEMPO (2.2 mg, 0.01 mmol). To the resulting biphasic system, which was cooled at 0° C., an aqueous solution of 0.35 M NaOCl (3.1 mL, 1.1 mmol) containing NaHCO$_3$ (0.25 g, 3 mmol) was added dropwise under vigorous stirring, at 0° C. over a period of 1 h. After the mixture had been stirred for a further 15 min at 0° C., ethyl acetate (10 mL) and H$_2$O (10 mL) were added. The aqueous layer was separated and washed with ethyl acetate (20 mL). The combined organic layers were washed consecutively with 5% aqueous citric acid (10 mL) containing KI (0.04 g), 10% aqueous Na$_2$S$_2$O$_3$ (10 mL), and brine and dried over Na$_2$SO$_4$. The solvents were evaporated under reduced pressure and the residue was purified by column-chromatography using chloroform as eluent.

Example 16

(S)-Methyl-2-(3-methyl-2-(2-oxohexadecanamido) butanamido)-acetate (4b)

Yield 73%; White solid; mp 118-119° C.; $[\alpha]_D$=−20.9 (c 1CHCl$_3$); $^1$H NMR (200 MHz, CDCl3) δ 7.46 (d, J=9.2 Hz, 1H), 6.53-6.37 (m, 1H), 4.24 (dd, Ji=6.6 Hz, J$_2$=9.2 Hz, 1H), 4.05 (dd, Ji=5.2, J$_2$=9.6 Hz, 2H), 3.77 (s, 3H), 2.91 (t, J=7.4 Hz, 2H), 2.22 (m, 1H), 1.61 (m, 2H), 1.26 (br s, 22H), 0.98 (t, J=5.8 Hz, 6H), 0.88 (t, J=6.6 Hz, 3H); $^{13}$C NMR (50 MHz, CDCl3) δ 198.3, 170.9, 170.0, 160.2, 58.6, 52.5, 41.1, 36.8, 31.9, 31.0, 29.6, 29.4, 29.3, 29.0, 23.1, 22.7, 19.2, 18.0, 14.1; Anal. Calcd for C$_{24}$H$_{44}$N$_2$O$_5$: C, 65.42; H, 10.07; N, 6.36. Found: C, 65.55; H, 9.97; N, 6.41.

Example 17

(S)-tert-Butyl-2-(3-methyl-2-(2-oxohexadecanamido)butanamido)-acetate (8b)

Yield 90%; White solid; mp 58-61° C.; $[\alpha]_D$=−17.2 (c 1CHCl3); $^1$H NMR (200 MHz, CDCl3) δ 7.50 (d, J=8.8 Hz, 1H), 6.59-6.45 (m, 1H), 4.34-3.18 (m, 1H), 4.01 (dd, Ji=18.2 Hz, J$_2$=5.4 Hz, 1H), 3.85 (dd, Ji=18.2 Hz, J$_2$=4.8 Hz, 1H), 2.89 (t, J=6.8 Hz, 2H), 2.28-2.19 (m, 1H), 1.64-1.48 (m, 2H), 1.45 (s, 9H), 1.24 (br s, 22H), 0.96 (t, J=5.8 Hz, 6H), 0.87 (t, J=6.6 Hz, 3H); $^{13}$C NMR (50 MHz, CDCl3) δ 198.3, 170.1, 168.5, 160.2, 82.4, 58.5, 41.9, 36.8, 31.9, 31.1, 29.6, 29.5, 29.4, 29.3, 29.0, 28.0, 23.1, 22.6, 19.2, 18.0, 14.1; MS (FAB): m/z (%): 483 (24) [M+H]$^+$; Anal. Calcd for C$_{27}$H$_{50}$N$_2$O$_5$: C, 67.18; H, 10.44; N, 5.80. Found: C, 67.31; H, 10.39; N, 5.68.

Example 19

General Method for the Cleavage of Tert-Butyl Protecting Group

A solution of the tert-butyl ester derivative (1 mmol) in 50% TFA/CH$_2$Cl$_2$ (10 mL) was stirred for 1 h at room temperature. The organic solvent was evaporated under reduced pressure. The residue was purified by recrystallization [ethyl acetate/petroleum ether (bp 40-60° C.)].

Example 20

(S)-2-(2-(2-Oxohexadecanamido)hexanamido)acetic Acid (9a)

Yield 61%; Colorless oil; $^1$H NMR (200 MHz, CDCl$_3$) δ 7.66 (d, J=8.8 Hz, 1H), 7.20-7.05 (m, 1H), 4.60-4.43 (m, 1H), 4.06 (d, J=3.6 Hz, 2H), 2.88 (t, J=3.8 Hz, 2H), 1.83-1.59 (m, 4H), 1.25 (br s, 26H), 0.89 (t, J=8.0 Hz, 6H); $^{13}$C NMR (50 MHz, CDCl$_3$) δ 198.1, 172.6, 171.4, 160.1, 53.0, 41.4, 36.9, 32.1, 31.9, 29.6, 29.4, 29.3, 29.0, 27.5, 23.0, 22.7, 22.3, 14.1, 13.8; MS (ESI): m/z (%): 442 (100) [M+H]$^+$; Anal. Calcd for C$_{24}$H$_{44}$N$_2$O$_5$: C, 65.42; H, 10.07; N, 6.36. Found: C, 65.19; H, 10.32; N, 6.25.

Example 21

(S)-2-(3-Methyl-2-(2-oxohexadecanamido)butanamido)acetic Acid (9b)

Yield 68%; White solid; mp 87-89° C.; $[\alpha]_D$=−1.8 (c 0.5 CHCl$_3$); $^1$H NMR (200 MHz, CDCl$_3$) δ 7.71 (d, J=9 Hz, 1H), 7.21-7.06 (m, 1H), 4.45-4.34 (m, 1H), 4.18-4.01 (m, 2H), 3.03-2.72 (m, 2H), 2.25-2.04 (m, 1H), 1.68-1.45 (m, 2H), 1.25 (br s, 22H), 0.97 (t, J=5.8 Hz, 6H), 0.88 (t, J=6.6 Hz, 3H); $^{13}$C NMR (50 MHz, CDCl$_3$) δ 198.0, 172.3, 170.9, 160.4, 58.6, 41.3, 36.9, 31.9, 31.1, 29.6, 29.4, 29.3, 29.0, 23.0, 22.7, 19.1, 18.1, 14.1; MS (ESI): m/z (%): 425 (100) [M−H]"; Anal. Calcd for C$_{23}$H$_{42}$N$_2$O$_5$: C, 64.76; H, 9.92; N, 6.57. Found: C, 64.65; H, 9.87; N, 6.63.

Example 22

(S)-2-(2-(2-oxohexadecanainido)hexyloxy)acetic Acid (18)

Yield 88%; White solid; mp 64-66° C.; $[a]_D$=−5.2 (c 0.5 CHCl3); $^1$H NMR (200 MHz, CDCl3) δ 7.32 (d, J=8.8 Hz, 1H), 4.14 (s, 2H), 4.07-3.95 (m, 1H), 3.66 (dd, $J_i$=9.6 Hz, $J_2$=4.8 Hz, 1H), 3.55 (dd, $J_i$=9.6 Hz, $J_2$=3.6 Hz, 1H), 2.90 (t, J=7.4 Hz, 2H), 1.75-1.46 (m, 4H), 1.25 (br s, 26H), 0.98-0.80 (m, 6H); $^{13}$C NMR (50 MHz, CDCl3) δ 199.1, 174.6, 160.2, 72.9, 67.8, 49.5, 36.8, 31.9, 30.8, 29.6, 29.4, 29.3, 29.0, 28.0, 23.2, 22.6, 22.4, 14.1, 13.9; MS (ESI): m/z (%): 450 (100) [M+Na]$^+$; Anal. Calcd for $C_{24}H_{45}NO_5$: C, 67.41, H, 10.61, N, 3.28. Found: C, 67.59, H, 10.64, N, 3.14.

Example 23

General Method for the Synthesis of Dipeptides

The dipeptides were prepared following the general methods described herein.

Example 24

(S)-Methyl 2-(2-(tert-butoxycarbonylamino)hexanamido)acetate (2a)

Yield 65%; White solid; mp 95-96° C.; $[a]_D$=−17.8 (c 1CHCl3); $^1$H NMR (200 MHz, CDCl3) δ 6.85-6.73 (m, 1H), 5.12 (d, J=8.2 Hz, 1H), 4.22-4.07 (m, 1H), 4.03 (d, J=5.6 Hz, 2H), 3.74 (s, 3H), 1.93-1.72 (m, 1H), 1.69-1.48 (m, 1H), 1.43 (s, 9H), 1.39-1.21 (m, 4H), 0.88 (t, J=6.6 Hz, 3H); $^{13}$C NMR (50 MHz, CDCl3) δ 172.6, 170.1, 155.7, 80.0, 54.4, 52.3, 41.0, 32.2, 28.2, 27.6, 22.3, 13.9.

Example 25

(S)-Methyl 2-(2-(tert-butoxycarbonylamino)-3-methylbutanamido)-acetate (2b)

Yield 73%; White solid; mp 104-106° C.; $[a]_D$=−15.7 (c 1CHCl3); $^1$H NMR (200 MHz, CDCl3) δ 6.64 (m, 1H), 5.09 (d, J=7.6 Hz, 1H), 4.06-3.96 (m, 3H), 3.76 (s, 3H), 2.19 (m, 1H), 1.42 (s, 9H), 0.99 (d, J=7.0 Hz, 3H), 0.94 (d, J=7.0 Hz, 3H); $^{13}$C NMR (50 MHz, CDCl3) δ 171.9, 170.1, 155.7, 80.0, 59.7, 52.3, 41.0, 30.8, 28.2, 19.2, 18.0. Anal. Calcd for $C_{13}H_{24}N_2O_5$: C, 54.15; H, 8.39; N, 9.72. Found: C, 53.92; H, 8.52; N, 9.61.

Example 26

(S)-Ethyl 2-(2-(tert-butoxycarbonylamino)hexanamido)acetate (2c)

Yield 69%; Oil; $[a]_D$=−14.8 (c 1CHCl3); $^1$H NMR (200 MHz, CDCl3) δ 7.00-6.85 (m, 1H), 5.23 (d, J=7.2 Hz, 1H), 4.22-4.05 (m, 3H), 4.02-3.93 (m, 2H), 1.91-1.69 (m, 1H), 1.66-1.45 (m, 1H), 1.40 (s, 9H), 1.35-1.18 (m, 7H), 0.86 (t, J=6.6 Hz, 3H); $^{13}$C NMR (50 MHz, CDCl3) δ 172.7, 169.6, 155.6, 79.8, 61.3, 54.3, 41.1, 32.3, 28.2, 27.5, 22.3, 14.0, 13.8.

Example 27

(S)-tert-Butyl 2-(2-(benzyloxycarbonylamino)hexanamido)acetate (6a)

Yield 64%; White solid; mp 80-82° C.; $[a]_D$=−8.4 (c 0.5 CHCl3); $^1$H NMR (200 MHz, CDCl3) δ 7.41-7.26 (m, 5H), 6.62-6.49 (m, 1H), 5.41 (d, J=8.0 Hz, 1H), 5.12 (s, 2H), 4.29-4.11 (m, 1H), 3.92 (d, J=4.6 Hz, 2H), 1.98-1.77 (m, 1H), 1.75-1.59 (m, 1H), 1.47 (s, 9H), 1.42-1.21 (m, 4H), 0.89 (t, J=7 Hz, 3H); $^{13}$C NMR (50 MHz, CDCl3) δ 171.9, 168.7, 156.1, 136.2, 128.5, 128.1, 128.0, 82.3, 67.0, 54.9, 42.0, 32.4, 28.0, 27.5, 22.3, 13.8. Anal. Calcd for $C_{20}H_{30}N_2O_5$: C, 63.47; H, 7.99; N, 7.40. Found: C, 63.28; H, 8.15; H, 7.28.

Example 28

(S)-tert-Butyl 2-(2-(benzyloxycarbonylamino)-3-methylbutanamido)-acetate (6b)

Yield 81%; White solid; mp 139-141° C.; $[a]_D$=−6.8 (c 0.5 CHCl$_3$); $^1$H NMR (200 MHz, CDCl3) δ 7.42-7.28 (m, 5H), 6.47-6.35 (m, 1H), 5.39 (d, J=8.6 Hz, 1H), 5.12 (s, 2H), 4.11-4.00 (m, 1H), 4.99-3.83 (m, 2H), 2.28-2.05 (m, 1H), 1.47 (s, 9H), 0.99 (d, J=7.0 Hz, 3H), 0.94 (d, J=7.0 Hz, 3H); $^{13}$C NMR (50 MHz, CDCl3) δ1712, 168.6, 156.0, 136.1, 128.5, 128.2, 128.0, 82.4, 67.1, 60.3, 42.0, 31.0, 28.0, 19.2, 17.6. Anal. Calcd for $C_{19}H_{28}N_2O_5$: C, 62.62; H, 7.74; N, 7.69. Found: C, 62.39; H, 7.91; N, 7.55.

Example 29

(S)-Ethyl 2-(2-(tert-butoxycarbonylamino)hexyloxy)acetate (11)

To as stirred solution of Boc-L-Nle-ol (0.50 g, 1.9 mmol) in dry tetrahydrofuran (15 mL), cooled at 0° C. under nitrogen, NaH (0.05 g, 2.1 mmol) was added. The reaction mixture was stirred for 45 min at 0° C., followed by addition of 18-crown-6 (0.25 g, 0.9 mmol) and subsequently a solution of ethyl bromoacetate (0.47 g, 2.8 mmol) in dry tetrahydrofuran (4 mL) was added dropwise at 0° C. The reaction mixture was stirred for 1 h at 0° C. and overnight at room temperature. The organic solvent was evaporated under reduced pressure and the residue was purified by column-chromatography using chloroform as eluent. Yield 55%; Oil; $[a]_D$=−13.9 (c 1CHCl3); $^1$H NMR (200 MHz, CDCl3) δ 4.85-4.78 (m, 1H), 4.17 (q, J=7.4 Hz, 2H), 4.03 (s, 2H), 3.72-3.58 (m, 1H), 3.56-3.41 (m, 2H), 1.62-1.21 (m, 18H), 0.85 (t, J=6.6 Hz, 3H); $^{13}$C NMR (50 MHz, CDCl3) δ 170.3, 155.6, 78.9, 73.3, 68.4, 60.7, 50.3, 31.5, 28.3, 28.1, 22.5, 14.1, 13.9. Anal. Calcd for $C_{15}H_{29}NO_5$: C, 59.38; H, 9.63; N, 4.62. Found: C, 59.16; H, 9.82; N, 4.51.

Example 30

(S)-tert-Butyl 2-(2-(benzyloxycarbonylamino)hexyloxy)acetate (15)

To a stirred solution of Z-L-Nle-ol (0.20 g, 0.8 mmol) in benzene (0.8 mL), tert-butyl bromoacetate (0.47 g, 2.4 mmol) and subsequently aqueous NaOH 50% (0.8 mL) and the phase transfer catalyst Bu$_4$NHSO$_4$ (0.07 g, 0.2 mmol) were added. The reaction mixture was vigorously stirred for 2 h. Ethyl acetate (10 mL) and H$_2$O (10 mL) were added and the aqueous layer was separated and extracted with ethyl acetate (2×10 mL). The combined organic layers were washed with brine and dried over Na$_2$SO$_4$. The organic solvent was evaporated under reduced pressure and the residue was purified by column-chromatography using petroleum ether (bp 40-60° C.)/ethyl acetate 8:2 as eluent. Yield 74%; Oil; $[a]_D$=−12.2 (c 1CHCl3); $^1$H NMR (200 MHz, CDCl3) δ 7.34-7.22 (m, 5H), 5.30 (d, J=8 Hz, 1H), 5.06 (s, 2H), 3.91 (s, 2H), 3.80-3.62 (m, 1H), 3.55 (dd, Ji=9.0 Hz, $J_2$=4.0 Hz, 1H), 3.46 (dd, Ji=9.2 Hz, $J_2$=4.2 Hz, 1H), 1.62-1.45 (m, 2H), 1.43 (s, 9H), 1.37-1.21 (m, 4H), 0.85 (t, J=6.8 Hz, 3H); $^{13}$C NMR (50 MHz, CDCl3) δ 169.5, 156.0, 136.6, 128.3, 128.0, 127.8, 81.5, 73.0, 68.7, 66.3, 50.9, 31.4, 28.0, 27.9, 22.4, 13.8. Anal. Calcd for $C_{20}H_{31}NO_5$: C, 65.73; H, 8.55; N, 3.83. Found: C, 65.52; H, 8.71; H, 3.70.

Example 31

In Vitro $PLA_2$ Assays

Phospholipase $A_2$ activity was determined using the previously described modified Dole assay with buffer and substrate conditions optimized for each enzyme as described previously: (i) GIVA $cPLA_2$ substrate mixed-micelles were composed of 400 µM Triton X-100, 97 µM PAPC, 1.8 µM $^{14}$C-labeled PAPC, and 3 µM $PIP_2$ in buffer containing 100 mM HEPES pH 7.5, 90 µM $CaCl_2$, 2 mM DTT and 0.1 mg/ml BSA; (ii) GVI $iPLA_2$ substrate mixed-micelles were composed of either (a) 400 µM Triton X-100, 99 µM DPPC, and 1.5 µM $^{14}$C-labeled DPPC in buffer containing 200 mM HEPES pH 7.0, 1 mM ATP, 2 mM DTT and 0.1 mg/ml BSA or (b) 400 µM Triton X-100, 98.3 µM PAPC, and 1.7 µM $^{14}$C-labeled PAPC in buffer containing 100 mM HEPES pH 7.5, 2 mM ATP and 4 mM DTT; and (iii) GV $sPLA_2$ substrate mixed-micelles were composed of 400 µM Triton X-100, 99 µM DPPC, and 1.5 µM $^{14}$C-labeled DPPC in buffer containing 50 mM Tris pH 8.0 and 5 mM $CaCl_2$.

Example 32

In Vitro $PLA_2$ Inhibition Studies

Initial screening of compounds at 0.091 mole fraction inhibitor in mixed-micelles was carried out. Compounds displaying 25% or less inhibition had no inhibitory affect (designated N.D.). The average percent inhibition (and standard error, n=3) for compounds displaying more than 25% and less than 90% enzyme inhibition is reported herein. If the percent inhibition was greater than 90%, then its $X_I(50)$ was determined by plotting percent inhibition vs. inhibitor molar fraction (7 points; typically 0.005 to 0.091 mole fraction). Inhibition curves were modeled in Graphpad Prism using either a linear (x, y intercept=0) or non-linear regression (one-site binding model—hyperbola, BMAX=100) to calculate the reported $X_I(50)$ and associated error values.

Example 33

Inhibition of Arachidonic Acid Release. RAW 264.7 Cell Culture and AA Quantitation RAW 264.7 macrophages were maintained in a humidified atmosphere at 37° C. with 5% $CO_2$, as described elsewhere.[36] The cells were cultured in DMEM media that was supplemented with 10% fetal bovine serum, 2 mM glutamine, 100 units/mL penicillin, 100 µg/ml streptomycin, and non-essential amino acids. The cells were plated at a confluency of $2\times10^6$ cells per well in 6 well tissue culture plates and allowed to adhere overnight. Inhibitors were added to the medium 30 min before $Kdo_2$-Lipid A was added and the supernatants were collected at 1 hour following stimulation. Subsequently, AA was extracted from the supernatants and quantitated by HPLC-MS, as described elsewhere.[36, 37] AA release levels were normalized to pmol AA release per million cells though DNA quantitation using the Broad Range DNA Quant-Kit (Invitrogen). $IC_{50}$ values were determined by estimating the concentration of inhibitor required for half maximal inhibition of the maximum inhibition observed with a given inhibitor.

REFERENCES

1. Schaloske, R. H.; Dennis, E. A. Biochim. Biophys. Acta 2006, 1761, 1246.
2. Kudo, I.; Murakami, M. Prostag. Oth. Lipid M. 2002, 68-69, 3.
3. Leslie, C. C. Prostaglandins Leukot. Essent. Fatty Acids 2004, 70, 373.
4. Mounier, C. M.; Ghomashchi, F.; Lindsay, M. R.; James, S.; Singer, A. G.; Parton, R. G.; Gelb, M. H. J. Biol. Chem. 2004, 279, 25024.
5. Satake, Y.; Diaz, B. L.; Balestrieri, B.; Lam, B. K.; Kanaoka, Y.; Grusby, M. J.; Arm, J. P. J. Biol. Chem. 2004, 279, 16488.
6. Shirai, Y.; Balsinde, J.; Dennis, E. A. Biochim. Biophys. Acta 2005, 1735, 119.
7. Winstead, M. V.; Balsinde, J.; Dennis, E. A. Biochim. Biophys. Acta 2000, 1488, 28.
8. Balsinde, J. Balboa, M. A. Cellular Signalling 2005, 17, 1052.
9. Magrioti, V.; Kokotos, G. Anti-Inflammatory Anti-Allergy Agents Med. Chem. 2006, 5, 189.
10. Lehr, M. Anti-Inflammatory Anti-Allergy Agents Med. Chem. 2006, 5, 149.
11. Reid, R. C. Curr. Med. Chem. 2005, 12, 3011.
12. Kokotos, G.; Kotsovolou, S.; Six, D. A.; Constantinou-Kokotou, V.; Beltzner, C. C.; and Dennis, E. A J. Med. Chem. 2002, 45, 2891.
13. Kokotos, G.; Six, D. A.; Loukas, V.; Smith T.; Constantinou-Kokotou, V.; Hadjipavlou-Litina D.; Kotsovolou, S.; Chiou, A.; Beltzner, C. C.; and Dennis, E. A. J. Med. Chem. 2004, 47, 3615.
14. Constantinou-Kokotou, V.; Peristeraki, A.; Kokotos, C. G.; Six, D. A.; Dennis, E. A. J. Pept. Sci. 2005, 11, 431.
15. Yaksh, T. L.; Kokotos, G.; Svensson, C. I.; Stephens, D.; Kokotos, C. G.; Fitzsimmons, B.; Hadjipavlou-Litina, D.; Hua, X.-Y.; Dennis, E. A. J. Pharmacol. Exp. Ther. 2006, 316, 466.
16. Stephens, D.; Barbayianni, E.; Constantinou-Kokotou, V.; Peristeraki, A.; Six, D. A.; Cooper, J.; Harkewicz, R.; Deems, R. A.; Dennis, E. A.; Kokotos, G. J. Med. Chem. 2006, 49, 2821.
17. Six, D. A.; Barbayianni, E.; Loukas, V.; Constantinou-Kokotou, V.; Hadjipavlou-Litina, D.; Stephens, D.; Wong, A. C.; Magrioti, V.; Moutevelis-Minakakis, P.; Baker, S.; Dennis, E. A.; Kokotos, G. J. Med. Chem. 2007, 50, 4222.
18. Moutevelis-Minakakis, P.; Neokosmidi, A.; Filippakou, M.; Stephens, D.; Dennis E. A.; Kokotos, G. J. Pept. Sci. 2007, 13, 634.
19. Antonopoulou, G.; Magrioti, V.; Stephens, D.; Constantinou-Kokotou, V.; Dennis E. A.; Kokotos, G. J. Pept. Sci. 2008, 14, 1111.
20. Antonopoulou, G.; Barbayianni, E.; Magrioti, V.; Cotton, N.; Stephens, D.; Constantinou-Kokotou, V.; Dennis, E. A.; Kokotos, G. Bioorg. Med. Chem., 2008, 16, 10257.
21. Spatola, A. F. In: Weinstein B. (ed) Chemistry and biochemistry of amino acids, peptides and proteins 1983, 7, Dekker, New York, 267.
22. Rubini, E.; Gilon, C.; Selinger, Z.; Chorev, M. Tetrahedron 1986, 42, 6039.
23. TenBrink, R. E.; Pals, D. T.; Harris, D. W.; Johnson, G. A. J. Med. Chem. 1988, 31, 671.
24. Ho, M.; Uhrin, A.; Huang, M. Bioorg. Med. Chem. Lett. 1994, 4, 553.
25. Roubini, E.; Laufer, R.; Gilon, C.; Selinger, Z.; Roques, B. P.; Chorev, M. J. Med. Chem. 1991, 34, 2430.

26. Hedenström, M.; Yuan, Z.; Brickmann, K.; Carlsson, Y.; Ekholm, K.; Johansson, B.; Kreutz, E.; Nilsson, A.; Sethson, I.; Kihlberg, J. J. Med. Chem. 2002, 45, 2501.
27. Sheehan, J. C.; Cruickshank, P. A.; Boshart, G. L. J. Org. Chem. 1961, 26, 2525.
28. Dess, D. B.; Martin, J. C. J. Am. Chem. Soc. 1991, 113, 7277.
29. Ma, Z.; Bobbitt, J. M. J. Org. Chem. 1991, 56, 6110.
30. Leanna, M. R.; Sowin, T. J.; Morton, H. E. Tetrahedron Lett. 1992, 33, 5029.
31. Kokotos, G. Synthesis 1990, 299.
32. Kokotos, G.; Noula, C. J. Org. Chem. 1996, 61, 6994.
33. Altmann, K.-H.; Chiesi, C. S.; Garcia-Echeverria, C. Bioorg. Med. Chem. Lett. 1997, 7, 1119.
34. Chiou, A.; Markidis, T.; Constantinou-Kokotou, V.; Verger, R.; Kokotos, G. Org. Lett. 2000, 2, 347.
35. Baskakis, C.; Magrioti, V.; Cotton, N.; Stephens, D.; Constantinou-Kokotou, V.; Dennis, E. A.; Kokotos, G. J. Med. Chem. 2008, 51, 8027-8037.
36. Buczynski, M. W.; Stephens, D. L.; Bowers-Gentry, R. C.; Grkovich, A.; Deems., R. A.; and Dennis, E. A. J. Biol. Chem. 2007, 282, 22834.
37. Deems, R. A.; Buczynski, M. W.; Bowers-Gentry, R. C.; Harkewicz, R.; Dennis, E. A. Methods Enzymol. 2007, 432, 59.
38. Pierson, M. E.; Comstock, J. M.; Simmons, R. D.; Kaiser, F.; Julien, R.; Zongrone, J.; Rosamond, J. D. J. Med. Chem. 1997, 40, 4302.
39. Mendre, C.; Rodriguez, M.; Laur, J.; Aumelas, A.; Martinez, J. Tetrahedron 1988, 44, 4415.
40. Johnson, R. L.; Bontems, R. J.; Yang, K. E.; Mishra, R. K. J. Med. Chem. 1990, 33, 1828.

All patents and other references cited in the specification are indicative of the level of skill of those skilled in the art to which the disclosure pertains, and are incorporated by reference in their entireties, including any tables and figures, to the same extent as if each reference had been incorporated by reference in its entirety individually.

One skilled in the art would readily appreciate that the present disclosure is well adapted to obtain the ends and advantages mentioned, as well as those inherent therein. The methods, variances, and compositions described herein as presently representative of preferred embodiments are exemplary and are not intended as limitations on the scope of the disclosure. Changes therein and other uses will occur to those skilled in the art, which are encompassed within the spirit of the disclosure, are defined by the scope of the claims.

Definitions provided herein are not intended to be limiting from the meaning commonly understood by one of skill in the art unless indicated otherwise. The disclosure described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure. Thus, it should be understood that although the present disclosure has been specifically disclosed by preferred embodiments and optional features, modification and variation of the disclosure embodied therein herein disclosed may be resorted to by those skilled in the art, and that such modifications and variations are considered to be within the scope of this disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein. Other embodiments are within the following claims. In addition, where features or aspects of the disclosure are described in terms of Markush groups, those skilled in the art will recognize that the disclosure is also thereby described in terms of any individual member or subgroup of members of the Markush group.

TABLE 1

Inhibition of PLA$_2$ by 2-oxoamides based on dipeptides and pseudodipeptides.[a]

| Compound | Structure | GIVA cPLA$_2$ | | GVIA iPLA$_2$ | | GV sPLA$_2$ | |
| --- | --- | --- | --- | --- | --- | --- | --- |
| | | X$_I$(50) | % inhibition | X$_I$(50) | % inhibition | X$_I$(50) | % inhibition |
| 4a | | 0.021 ± 0.009 | | 0.045 ± 0.018 | | | 65 |
| 4b | | | 25 | | N.D.[a] | | N.D.[a] |

TABLE 1-continued

Inhibition of PLA$_2$ by 2-oxoamides based on dipeptides and pseudodipeptides.[a]

| Compound | Structure | GIVA cPLA$_2$ X$_I$(50) | % inhibition | GVIA iPLA$_2$ X$_I$(50) | % inhibition | GV sPLA$_2$ X$_I$(50) | % inhibition |
|---|---|---|---|---|---|---|---|
| 4c | | | 73 | 0.020 ± 0.002 | | | 63 |
| 8a | | | 72 | 0.011 ± 0.001 | | | 59 |
| 8b | | 0.028 ± 0.015 | | 0.044 ± 0.025 | | | 78 |
| 9a | | 0.035 ± 0.014 | | | N.D.[a] | | N.D.[a] |
| 9b | | 0.061 ± 0.017 | | | N.D.[a] | | N.D.[a] |
| 13 | | | 52 | 0.017 ± 0.002 | | | 81 |
| 17 | | | 44 | | 81 | | 57 |
| 18 | | 0.017 ± 0.002 | | | N.D.[a] | | N.D.[a] |

TABLE 1-continued

Inhibition of PLA$_2$ by 2-oxoamides based on dipeptides and pseudodipeptides.[a]

| Compound | Structure | GIVA cPLA$_2$ X$_1$(50) | % inhibition | GVIA iPLA$_2$ X$_1$(50) | % inhibition | GV sPLA$_2$ X$_1$(50) | % inhibition |
|---|---|---|---|---|---|---|---|
| AX006 | (structure) | 0.024 ± 0.015[b] | | N.D.[a,b] | | | |
| AX048 | (structure) | 0.022 ± 0.009[b] | | 0.027 ± 0.009[b] | | | |

[a]Average percent inhibition and standard error (n = 3) reported for each compound at 0.091 mole fraction. N.D. signifies compounds with less than 25% inhibition (or no detectable inhibition).
[b]Data taken from ref 15.

TABLE 2

Effect of 2-oxoamide inhibitors on Kdo$_2$-Lipid A stimulated AA release from RAW 264.7 macrophages.

| Compound | Structure | AA Release Inhibition (%) |
|---|---|---|
| 19 | (structure) | 52 ± 5 |
| 20 | (structure) | 56 ± 6 |
| 21 | (structure) | 27 ± 6 |
| 22 | (structure) | Activation |
| 23 | (structure) | Activation |
| 24 | (structure) | Activation |
| 25 | (structure) | 62 ± 5 |
| 26 | (structure) | 79 ± 0.5 |

TABLE 2-continued

Effect of 2-oxoamide inhibitors on Kdo$_2$-Lipid A stimulated AA release from RAW 264.7 macrophages.

| Compound | Structure | AA Release Inhibition (%) |
|---|---|---|
| 27 | | Activation |
| 28 | | 6 ± 10 |
| 8b | | 30 ± 2 |
| 29 | | Activation |
| 30 | | 74 ± 8 |
| 31 | | Activation |

TABLE 3

IC$_{50}$ values for the inhibition of arachidonic acid release.

| Compound | Structure | IC$_{50}$ (μM) |
|---|---|---|
| 19 | | 25 |
| 20 | | 10 |
| 25 | | 25 |
| 26 | | 25 |
| 30 | | 25 |
| 35 | | 7 |
| 18 | | 2 |

What is claimed is:
1. A compound selected from the group consisting of: a compound having the structural formula or a pharmaceutically acceptable salt or solvate thereof, wherein:

X is $CH_2$, O, NH or $N(C_1-C_6)$alkyl;
Y and Z form CONH or $CH_2O$;
$R^1$ and $R^2$ are each independently hydrogen, a side chain of a natural amino acid, a linear, branched or cyclic alkyl, a linear, branched or cyclic alkenyl, a linear, branched or cyclic alkynyl, or substituted or unsubstituted aryl;
$R^3$ is hydrogen or $(C_1-C_1)$alkyl;
the Activated Carbonyl Group is and a compound having the structural formula or a pharmaceutically acceptable salt or solvate thereof, wherein:
X is $CH_2$, O, NH or $N(C_1-C_6)$alkyl;
Y and Z form CONH or $CH_2O$;
$R^1$ is hydrogen, a side chain of a natural amino acid, a linear, branched or cyclic alkyl, a linear, branched or cyclic alkenyl, a linear, branched or cyclic alkynyl, or substituted or unsubstituted aryl;
$R^3$ is hydrogen or $(C_1-C_6)$alkyl, and
$R^4$ is a linear, branched or cyclic alkyl, a linear, branched or cyclic alkenyl, a linear, branched or cyclic alkynyl, or substituted or unsubstituted aryl.

2. A pharmaceutical composition for use in inhibiting the enzymatic activity of phospholipase $A_2$ in a cell or organism, comprising a pharmaceutically acceptable carrier and a compound of claim 1.

3. The pharmaceutical composition according to claim 2, wherein the enzymatic activity inhibited is of phospholipase $cPLA_2$, $iPLA_2$ or $sPLA_2$.

4. The pharmaceutical composition according to claim 1, wherein the compound is

5. A compound of structural formula:

6. The pharmaceutical composition of claim 2, wherein the composition further inhibits cellular release of arachidonic acid.

7. A method for modulating the effects of inflammatory processes in a mammal, comprising administering an effective amount of the compound of claim 1.

8. The method according to claim 7, wherein the mammal is a human.

9. A method of inhibiting the enzymatic activity of phospholipase $A_2$ in a cell or organism, comprising contacting the cell or organism with a compound of claim 5.

* * * * *